US011497469B2

(12) United States Patent
Rijken et al.

(10) Patent No.: US 11,497,469 B2
(45) Date of Patent: Nov. 15, 2022

(54) COOLABLE ULTRASOUND PROBE AND ULTRASOUND SYSTEM

(71) Applicant: KONINKLIJKE PHILIPS N.V., Eindhoven (NL)

(72) Inventors: Antonius Maria Rijken, Eindhoven (NL); David Andrew Fish, Worthing (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 475 days.

(21) Appl. No.: 16/306,877

(22) PCT Filed: Jun. 5, 2017

(86) PCT No.: PCT/EP2017/063595
§ 371 (c)(1),
(2) Date: Dec. 3, 2018

(87) PCT Pub. No.: WO2017/211754
PCT Pub. Date: Dec. 14, 2017

(65) Prior Publication Data
US 2021/0030396 A1     Feb. 4, 2021

(30) Foreign Application Priority Data

Jun. 9, 2016   (EP) .................... 16173706

(51) Int. Cl.
*A61B 8/00*     (2006.01)
*A61N 7/00*     (2006.01)

(52) U.S. Cl.
CPC .......... *A61B 8/4444* (2013.01); *A61B 8/4272* (2013.01); *A61B 8/4477* (2013.01);
(Continued)

(58) Field of Classification Search
CPC ... A61B 8/4444; A61B 8/4477; A61B 8/4483; A61B 8/42; A61B 8/4272; A61B 8/546;
(Continued)

(56) References Cited

U.S. PATENT DOCUMENTS 5,955,823 A * 9/1999 Nilsson ................. B06B 1/0611
                                                 310/346
6,132,378 A * 10/2000 Marino ................ A61B 8/4281
                                                 600/459
(Continued)

FOREIGN PATENT DOCUMENTS

CN     101234030 A    8/2008
CN     101468240 A    7/2009
(Continued)

OTHER PUBLICATIONS

International Search and Written Opinion for International Application Serial No. PCT/EP2017/063595, 13 pages.

*Primary Examiner* — Christopher Koharski
*Assistant Examiner* — Taylor Deutsch (57) ABSTRACT

An ultrasound probe including a probe body having a mounting area and a flexible lip around said mounting area for sealing a space between the mounting area and a subject contacted by the ultrasound probe; and a number of ultrasound transducer elements mounted in the mounting area. The probe body further includes an inlet to said space and an outlet from said space for facilitating a fluid flow through said space when sealed. Also included are an ultrasound system including such an ultrasound probe and a method of subjecting a subject to ultrasound waves generated with such an ultrasound probe.

21 Claims, 9 Drawing Sheets

(52) U.S. Cl.
CPC ............ *A61B 8/4483* (2013.01); *A61B 8/546* (2013.01); *A61N 7/00* (2013.01); *A61N 2007/0052* (2013.01); *A61N 2007/0078* (2013.01)

(58) Field of Classification Search
CPC .... A61N 2007/0052; A61N 2007/0078; A61N 7/00; A61N 7/02; G01S 15/8915; G01S 7/5205; G01S 7/52079
See application file for complete search history.

(56) References Cited

U.S. PATENT DOCUMENTS

| | | | |
|---|---|---|---|
| 6,177,755 B1 * | 1/2001 | Hur | G10K 11/004 310/346 |
| 6,500,141 B1 | 12/2002 | Irion et al. | |
| 6,626,855 B1 | 9/2003 | Weng et al. | |
| 2005/0060012 A1 * | 3/2005 | Voorhees | A61F 7/02 607/96 |
| 2006/0235303 A1 | 10/2006 | Vaezy et al. | |
| 2007/0232923 A1 | 10/2007 | Asuri | |
| 2007/0242567 A1 | 10/2007 | Daft et al. | |
| 2008/0077056 A1 * | 3/2008 | Kagosaki | A61B 8/00 601/2 |
| 2008/0146924 A1 | 6/2008 | Smith et al. | |
| 2009/0036773 A1 * | 2/2009 | Lau | A61B 17/2202 600/439 |
| 2009/0112098 A1 | 4/2009 | Vaezy et al. | |
| 2009/0209863 A1 | 8/2009 | Haveri | |
| 2011/0072970 A1 | 3/2011 | Slobodzian et al. | |
| 2011/0077558 A1 * | 3/2011 | Ostrovsky | A61N 7/022 601/2 |
| 2011/0230767 A1 * | 9/2011 | Miyajima | A61B 8/00 600/459 |
| 2012/0223618 A1 | 9/2012 | Clark et al. | |
| 2013/0165005 A1 * | 6/2013 | Berard-Andersen | C09J 7/21 442/65 |
| 2013/0197555 A1 | 8/2013 | Schaer | |
| 2013/0242705 A1 * | 9/2013 | Kim | H04R 31/00 367/181 |
| 2014/0018661 A1 * | 1/2014 | Tsujita | A61B 5/0095 600/407 |
| 2014/0069194 A1 * | 3/2014 | Kim | G10K 11/002 73/632 |
| 2015/0045670 A1 | 2/2015 | Davidson et al. | |
| 2015/0045723 A1 | 2/2015 | Paithankar et al. | |
| 2015/0182200 A1 * | 7/2015 | Birglehner | A61B 8/4444 600/459 |
| 2015/0257779 A1 | 9/2015 | Sinelnikov et al. | |
| 2016/0089551 A1 | 3/2016 | Ylihautala et al. | |
| 2018/0161603 A1 * | 6/2018 | Seip | A61B 8/546 |

FOREIGN PATENT DOCUMENTS

| | | | |
|---|---|---|---|
| CN | 101217772 B | 11/2010 | |
| CN | 203075484 A | 7/2013 | |
| CN | 103549939 A | 2/2014 | |
| CN | 105209119 A | 12/2015 | |
| EP | 2226099 A1 * | 9/2010 | ............... A61N 7/00 |
| WO | WO-0078232 A1 * | 12/2000 | ............... A61N 7/02 |
| WO | 2011055315 A1 | 5/2011 | |

* cited by examiner

COOLABLE ULTRASOUND PROBE AND ULTRASOUND SYSTEM

This application is the U.S. National Phase application under 35 U.S.C. § 371 of International Application No. PCT/EP2017/063595, filed on Jun. 5, 2017, which claims the benefit of European Application Serial No. 16173706.9, filed Jun. 9, 2016. These applications are hereby incorporated by reference herein.

FIELD OF THE INVENTION

The present invention relates to an ultrasound probe comprising a probe body having a mounting area and a plurality of ultrasound transducer elements mounted in the mounting area.

The present invention further relates to an ultrasound system comprising such an ultrasound probe.

The present invention further relates to a method of subjecting a subject to ultrasound waves generated with such an ultrasound probe.

BACKGROUND OF THE INVENTION

Ultrasound waves find several applications in medicine. One such application is ultrasound imaging, wherein ultrasound waves are emitted by an ultrasound device comprising an array of ultrasound transducers into the body of a patient and echoes of the ultrasound waves are collected by the ultrasound transducers or by dedicated ultrasound receivers and processed to generate an ultrasound image, e.g. a 1D, 2D or 3D ultrasound image. Another application is ultrasound therapy such as high intensity focused ultrasound (HIFU) therapy in which ultrasound beams are generated by an ultrasound device comprising ultrasound transducer element tiles and are focused on diseased tissue. The significant energy deposition at the focus creates local temperatures in the range of about 65° C. to 85° C., which destroys the deceased tissue by coagulative necrosis.

Such ultrasound systems typically comprise an ultrasound probe for delivering ultrasound waves to a subject, e.g. to a patient being imaged or treated. Such an ultrasound probe typically comprises a plurality of ultrasound transducers such as piezoelectric transducer elements formed of materials such as lead zirconate titanate (PZT) or polyvinylidene-fluoride (PVDF) and capacitive micro-machined ultrasonic transducer (CMUT) elements in which a membrane including a first electrode over a cavity comprising a second electrode opposite the first electrode and separated therefrom by the cavity is used to generate the ultrasound waves (or receive the ultrasound waves in a receive mode) through application of an appropriate stimulus, e.g. an alternating current, to the first and second electrodes. Increasingly, several of such ultrasound transducer elements are combined on so-called tiles, e.g. chips of a semiconductor substrate in which the ultrasound transducer elements, which tiles may have dimensions of several centimetres squared in some applications. This allows for the ultrasound probes to cover larger areas of the subject's body to be imaged or treated. The ultrasound transducer elements of such tiles may be grouped together and operated in unison, such that the tile behaves as a composite ultrasound transducer element comprising multiple facets, i.e. ultrasound transducer cells combining to form the composite ultrasound transducer element, or alternatively may be operated independently.

For such ultrasound probes, and in particular for large area ultrasound probes, e.g. ultrasound probes comprising a plurality of such ultrasound transducer tiles, it is far from trivial to establish a good contact between the ultrasound probe and the part of the body to be imaged. For smaller ultrasound probes, this is typically achieved by using special gels that improve the contact between the ultrasound transducer array and the body part. However, a drawback of this approach is that usually large amounts of gel have to be used, which may contain air bubbles that interfere with the transmission or reception of the ultrasound signals. Also, such gel applications may no longer be practically feasible for large area ultrasound probes.

To this end, the ultrasound probe may be designed such that upon contact with the subject's body, the ultrasound transducer elements are sealed against the subject's body, e.g. by the creation of a sealed space between the ultrasound transducer elements and the subject's body in which an underpressure is created relative to ambient pressure, e.g. by forcing some of the air from between the ultrasound probe and the subject's body through pressing the ultrasound probe onto the body. This creates a suction effect between the ultrasound probe and the subject's body that promotes the retention of the ultrasound probe in the desired location on the subject's body.

A drawback of this approach is that a stationary volume of a fluid, e.g. air, is trapped between the ultrasound probe and the subject's body, the temperature of which will increase during transmission of the ultrasound waves with the ultrasound probe as this fluid is heated by the transmitted ultrasound waves. This heat can be transferred to the ultrasound transducer elements, which as a result may be prone to overheating. A temperature monitor in the ultrasound probe may monitor the temperature of the ultrasound transducer elements and may switch the ultrasound transducer elements to a low power mode for a period of time to prevent such overheating from occurring. However, such a low power mode may be undesirable in terms of ultrasound image quality, which is typically compromised in such a low power mode, whereas such a low power mode may prevent the generation of sufficient heat in the tissue to be treated with a HIFU ultrasound therapy system.

US 2012/223618 A1 discloses a curved high intensity focused ultrasound (HIFU) transducer comprising a curved piezoelectric array having opposite convex and concave back surfaces, the front surface comprising an acoustic transmitting surface, and a plurality of electrodes located on the convex back surface for applying electrical transmit signals to the array, and a printed circuit board spaced apart from and in opposition to the back surface of the curved piezoelectric array which couples electrical signals to the electrodes of the array, the space between the printed circuit board and the curved piezoelectric array comprising an acoustic air backing passageway of the piezoelectric array for air-cooling the curved piezoelectric array and the printed circuit board. This arrangement is however less suitable for compensating heating of the curved piezoelectric array by air trapped between the curved piezoelectric array and a subject's body.

SUMMARY OF THE INVENTION

The present invention seeks to provide an ultrasound probe that can prevent overheating of a fluid such as air trapped between the ultrasound transducer elements and the subject's body.

The present invention further seeks to provide an ultrasound system comprising such an ultrasound probe.

The present invention yet further seeks to provide a method of generating ultrasound waves using such an ultrasound probe.

According to an aspect, there is provided an ultrasound probe comprising a probe body having a mounting area and a flexible lip around said mounting area for sealing a space between the mounting area and a part of a subject opposite the mounting area when the subject is contacted by the ultrasound probe to facilitate the creation of a reduced pressure in said space; and
a plurality of ultrasound transducer elements mounted in the mounting area; wherein the probe body further comprises an inlet to said space and an outlet from said space for facilitating an air flow through said space when sealed, wherein, in order to create said reduced pressure upon the outlet being fluidly connected to a fluid displacement apparatus, the inlet is dimensioned to regulate said fluid flow compared to the fluid flow through the outlet or the inlet comprises a fluid flow regulator for regulating said air flow such that an air flow rate through the inlet is smaller than an air flow rate through the outlet at least at ambient pressure in said space.

Such an ultrasound probe facilitates the transport of fluid, e.g. air from the sealed surface during use, e.g. during ultrasound imaging or therapy of the subject, thereby transferring the heat generated by the ultrasound transducer elements and reducing the risk of such elements overheating during use. This also makes it possible to create an underpressure in the sealed space when an air displacement apparatus in fluid connection with the outlet has a greater fluid flow capacity as the flow-restricted inlet, to secure the probe against the subject's (body) part. Hence, the ultrasound probe advantageously uses the inlet and outlet for dual purposes, namely to provide a cooling air flow as well as to establish a reduced pressure in the space between the mounting area and the subject, which is achieved by controlling the respective air flow rates through the inlet and outlet, thereby obviating the need for separate inlets and outlets for cooling and reduced pressure creation. It is further noted that the provision of a reduced pressure is typically practically impossible when using liquids as coolants as such liquids can interfere with the outlet through which the reduced pressure is created.

The probe body may be flexible to facilitate a good conformal contact between the ultrasound probe and the subject over the full area of the probe body. For example, the probe body may be made of an elastomer such as a polysiloxane rubber or the like. The flexible lip may form an integral part of the probe body, i.e. may be made of the same material as the probe body.

At least one of the inlet and the outlet may be located in the flexible lip to provide access to the sealed space during use of the ultrasound probe.

In an embodiment, the plurality of ultrasound transducer elements are grouped on one or more ultrasound transducer tiles. In this embodiment, the ultrasound probe may be a large area probe for covering an area of the subject of at least 10 cm$^2$, preferably at least 100 cm$^2$. Such a large area ultrasound probe may be very effective in imaging or treating large areas of the subject's body.

According to another aspect, there is provided an ultrasound system comprising the ultrasound probe of any of the aforementioned embodiments and a fluid displacement apparatus fluidly connected to the outlet and arranged to generate the fluid flow through said space when sealed. Such a system may be operated for prolonged period of times without risk of overheating the ultrasound transducer elements, e.g. the ultrasound transducer tiles, due to the fact that the heat generated by such elements causing heating of the fluid in the sealed space is displaced by the fluid displacement apparatus and replaced with (ambient) fluid drawn into the sealed space through the inlet, such that the temperature of the fluid in the sealed space is better controlled. Such a fluid displacement apparatus may be a fan or a pump, e.g. a vacuum pump. In case of a vacuum pump, such a pump may be integral to a dwelling in which the ultrasound probe is deployed, e.g. a house vacuum or the like.

The ultrasound system of claim may further comprise a pressure reducing valve between the outlet and the fluid displacement apparatus in order to control the pressure, e.g an underpressure relative to ambient, in the sealed space.

In an embodiment, the ultrasound system further comprises a cooling apparatus fluidly coupled between the fluid displacement apparatus and the inlet. In such a closed loop arrangement, a volume of fluid may be circulated through the closed loop and cooled with the cooling apparatus to control the temperature of the fluid. In this embodiment, the fluid may be air. Alternatively, the cooling apparatus or the fluid displacement apparatus may be adapted to fill the space with a fluid when sealed, e.g. an inert fluid such as helium or nitrogen. The probe body may comprise a further outlet to said space, with the ultrasound system further comprising a further fluid displacement apparatus fluidly connected to the further outlet and adapted to maintain a reduced pressure in said space when sealed.

According to yet another aspect, there is provided a method of subjecting a subject to ultrasound waves generated with the ultrasound probe of any of the aforementioned embodiments, the method comprising positioning the ultrasound probe on the subject such that the space between the mounting area and the subject is sealed by the flexible lip; generating a reduced pressure in said sealed space; generating the ultrasound waves; and generating a fluid flow through the inlet to said sealed space and the outlet from said sealed space during the generation of the ultrasound waves. In this manner, the subject may be subjected to the ultrasound waves for a prolonged period of time without risking overheating of the ultrasound transducer elements of the ultrasound probe, thereby avoiding the need to periodically switch the ultrasound probe to a lower power mode to compensate for such overheating effects whilst at the same time securing the probe against the subject with the reduced pressure.

The method may further comprise cooling the fluid flow received from the sealed space through the outlet; and returning the cooled fluid flow to the sealed space through the inlet in order to further improve the temperature control over the temperature of the ultrasound transducer elements.

The method may further comprise inserting a fluid into the sealed space prior to cooling the fluid flow, for example to create an inert atmosphere in the sealed space and/or to insert a fluid into the sealed space having desirable heat transfer characteristics.

Preferably, the method further comprises maintaining a reduced pressure in the sealed space during the generation of the ultrasound waves in order to achieve a stable conformal contact between the ultrasound probe and the subject.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

In the context of the present application, an ultrasound transducer element tile is a discrete element, which may comprise any suitable type and number of ultrasound transducer elements; for example, the ultrasound transducer elements may be capacitive micromachined ultrasound transducer elements (CMUTs). The ultrasound transducer element tile for example may be a chip or the like of a semiconductor substrate such as a silicon substrate carrying circuitry including one or more ultrasound transducer elements. Each tile may comprise a plurality of CMUTs, e.g. organized as sub-arrays. Such tiles may have any suitable dimensions, e.g. the tiles may be square tiles having an area of several cm squared, e.g. may have dimensions of 2×2 cm, by way of non-limiting example. Such sizes allow for the simplification of beamforming processing because a regular active aperture of the ultrasound beam fits onto one tile and only one orientation position (of said tile) needs to be taking into account during the image reconstruction. Further, the aperture can either change its active size or "slide" to another tile during an anatomy scan.

Figure 1:
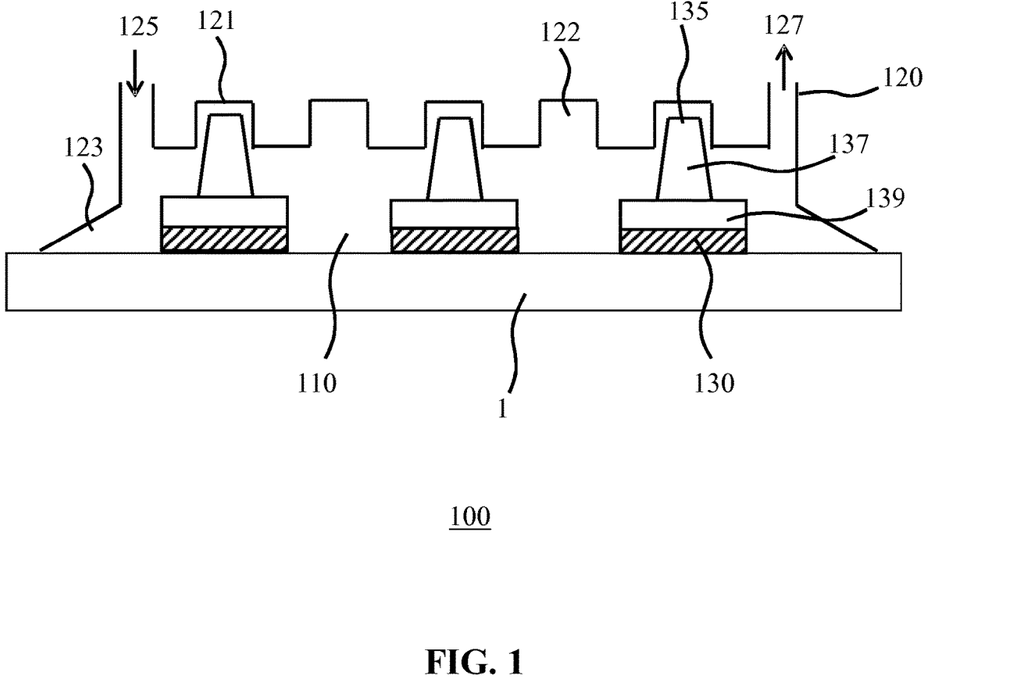
FIG. 1 schematically depicts a cross-sectional view of an ultrasound probe according to an embodiment.

FIG. 1 shows an example embodiment of an ultrasound probe 100 having a transducer array comprising ultrasound transducer element tiles 130 comprising one or more ultrasound transducer elements (not shown). Each tile 130 for example may be a diced chip or the like onto which the one or more ultrasound transducer elements have been formed or mounted. In the present invention, the ultrasound transducer elements may be implemented in any suitable manner. For example, the ultrasound transducer elements may be implemented by a piezoelectric ceramic material such as a lead zirconate titanate (PZT)-based material, a piezoelectric single crystal or composite material, a capacitive micromachined ultrasound transducer (CMUT) and so on. The ultrasound transducer element tiles 130 may have any suitable shape, e.g. a circular shape or polygonal shape. A polygonal shape such as a rectangular, e.g. square, shape is particularly mentioned as such a shape facilitates a close packing of the ultrasound transducer element tiles 130 within the transducer array, wherein the gap between adjacent ultrasound transducer element tiles 130 is minimized. The avoidance of relatively large gaps between adjacent ultrasound transducer element tiles 130 ensures that a substantially continuous image may be generated with the ultrasound probe 100 and may at least reduce the formation of ultrasound artefacts such as grating lobes. The transducer array may have any suitable shape, e.g. may be a 1-dimensional or 2-dimensional transducer array. Alternatively, the transducer array may be composed of individual ultrasound transducer elements. In a preferred embodiment, the ultrasound probe 100 comprises a plurality of ultrasound transducer tiles 130, each having a transducer surface area of several $cm^2$, e.g. 2-50 $cm^2$, to form a large area ultrasound probe 100.

Figure 2:
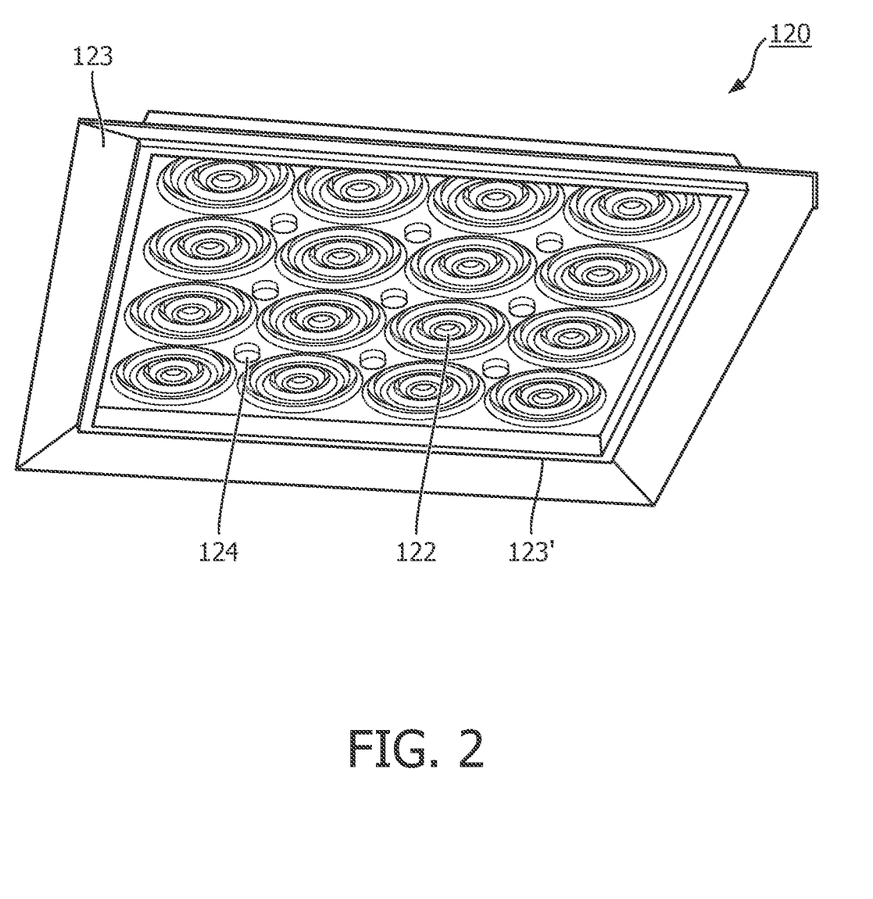
FIG. 2 schematically depicts a perspective view of a further aspect of the ultrasound probe according to FIG. 1.

The ultrasound probe 100 typically comprises a probe body 120 having a mounting region 121 onto which the ultrasound transducer element tiles 130 are mounted. A detail of such a probe body 120 is schematically depicted in FIG. 2. Although not shown, the transducer surfaces of the ultrasound transducer element tiles 130 may be covered by an acoustic layer, sometimes referred to as an acoustic window, in order to protect the ultrasound transducer array from being directly contactable, thereby protecting the transducer array from damage, as well as to protect the body of a subject 1, e.g. a patient, to be exposed to the ultrasound waves to be generated by the transducer array from being directly contacted by the transducer array, e.g. to protect the body from accidental electrical shock. As is well-known per se, such an acoustic window may further provide impedance matching between the transducer array and the body. The acoustic layer may be made of any material or combinations of materials known to the skilled person for such purposes.

The ultrasound probe 100 typically comprises a probe body 120 having a mounting region 121 onto which the ultrasound transducer element tiles 130 are mounted. A detail of such a probe body 120 is schematically depicted in FIG. 2. Although not shown, the transducer surfaces of the ultrasound transducer element tiles 130 may be covered by an acoustic layer, sometimes referred to as an acoustic window, in order to protect the ultrasound transducer array from being directly contactable, thereby protecting the transducer array from damage, as well as to protect the body of the subject 1, e.g. a patient, to be exposed to the ultrasound waves to be generated by the transducer array from being directly contacted by the transducer array, e.g. to protect the body from accidental electrical shock. As is well-known per se, such an acoustic window may further provide impedance matching between the transducer array and the body. The acoustic layer may be made of any material or combinations of materials known to the skilled person for such purposes.

The mounting region 121 of the probe body 120 may be rigid, e.g. may be a rigid carrier of the ultrasound transducer element tiles 130. Any suitable rigid material may be used for this purpose. Alternatively, the mounting region 121 may be flexible, which has the advantage that the mounting region 121 carrying the ultrasound transducer element tiles 130 may be deformed, e.g. to conform to a non-planar surface such as a contoured body of a patient to improve the quality of contact between the ultrasound transducer element tiles 130 and the patient's body. This is particularly relevant in case of large area ultrasound probes 100, where the probe may need to conform to a large area of the patient's body, e.g. an area of several tens or hundreds of $cm^2$. For example, the mounting region 121 may comprise an elastomer, i.e. a rubbery material, to provide the mounting region 121 with the desired flexibility. Examples of such an elastomer include a polyolefin, a diene polymer or a polysiloxane such as PDMS, a co-polymer or block-copolymer comprising a polyolefin, a diene polymer or a polysiloxane or a blend thereof although embodiments are not limited thereto. Polybutadiene, polydimethylsiloxane (PDMS) and relatively soft polyether block amides (PEBA) commonly used in catheters, are specifically mentioned. A medical grade PDMS is particularly preferred. For example, the ultrasound probe 100 may be implemented as a flexible mat for conforming to the surface (body) of the subject 1.

Figure 3:
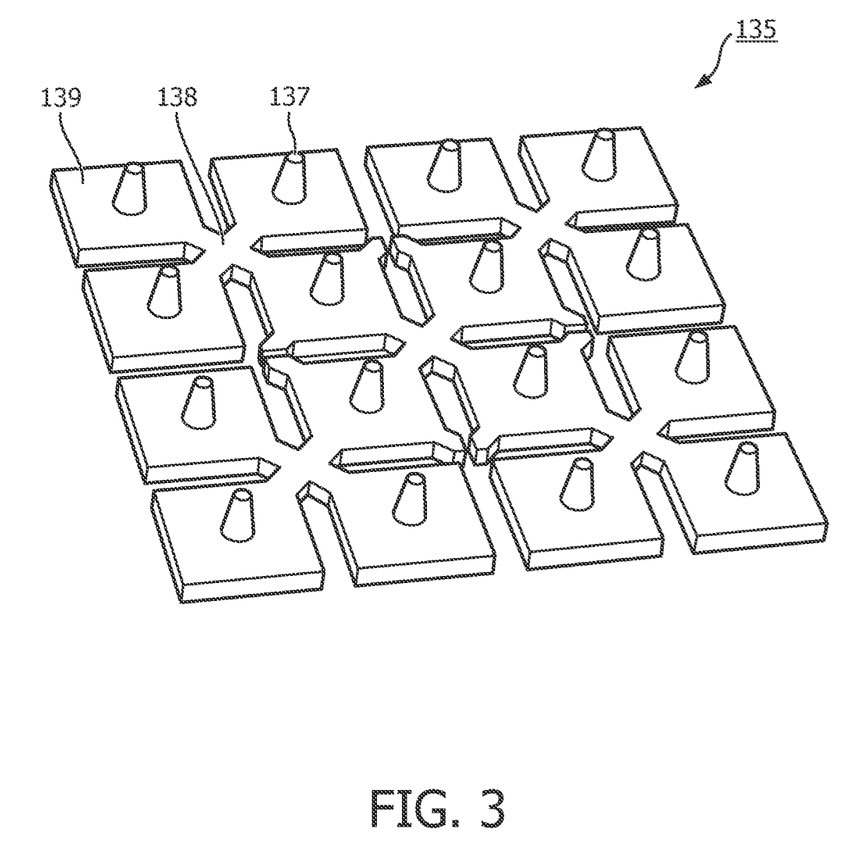
FIG. 3 schematically depicts a perspective view of a yet a further aspect of the ultrasound probe according to FIG. 1.

The ultrasound transducer element tiles 130 may be directly mounted onto the mounting region 121 in some embodiments (not shown). In alternative embodiments, such as the embodiment schematically depicted in FIG. 1, the mounting region 121 may comprise a plurality of receiving portions 122 for receiving a support member 135 onto which an ultrasound transducer element tile 130 may be mounted. A detail of such a support member 135 is schematically depicted in FIG. 3. The support members 135 may each comprise a pillar 137 that fits into one of the receiving portions 122 of the mounting region 121. Each pillar 137 carries a mounting portion 139 onto which the ultrasound transducer element tile 130 may be mounted. The support member 135 may be made of a flexible material, e.g. a rubber-like material, and may have interconnected mounting portions 139, e.g. in the form of a flexible mat through interconnecting regions 138 in between adjacent mounting portions 139.

As shown in FIG. 3, each interconnecting region 138 groups four quadrants of mounting portions 139 that each have a corner interconnected to the interconnecting region 138. In this manner, each tile 130 will exhibit at least two degrees of rotational freedom, such that a good conformal contact with the body of the subject 1 can be achieved when the pressure in a space 110 is reduced by evacuation of a portion of air as explained in more detail below, with the resulting downward force on the mounting portions 139 as transferred through the pillars 137 being translated into the desired conformal contact of the tiles 130 through these rotational degrees of freedom. In an alternative embodiment, the support member 135 may be a rigid member in which the mounting regions 139 are mounted on a flexible joint, e.g. a universal joint, a ball and socket joint, or the like.

The mounting region 121 is typically delimited by a flexible lip 123 that is arranged to contact the subject 1 upon placement of the ultrasound probe 100 on the subject 1. The lip 123 is flexible such that upon placement of the ultrasound probe 100 on the subject 1, the lip 123 seals a space 110 in between the mounting region 121 of the probe body 120 and the part of the subject's body opposite the mounting region 121. The mounting region 121 may be corrugated as schematically depicted in FIG. 1 such that the mounting region can act as a spring. Consequently, when air is evacuated from the space 110 to create an underpressure in the space 110, the atmospheric pressure over the probe 100 forces the sprung mounting region 121 against the body. As little as a 10% reduction in pressure in the space 110 may suffice to achieve a downward pressure of 1N/cm$^2$ on the mounting region 121. The sealing of the probe 100 onto the body may further be aided by a coupling gel, which for instance may be applied around the lip 123 only.

The lip 123 may form an integral part of the probe body 120, or may be adhered or otherwise attached to the mounting region 121. In the context of the present application, the lip 123 may have any suitable shape that facilitates the formation of a sealed space 110 in between the ultrasound transducer element tiles 130 and the body of the subject 1 upon placement of the ultrasound probe 100 on this body. The flexible lip 123 may be made of any suitable material, e.g. an elastomer as described above. In an embodiment, the mounting region 121 and the flexible lip 123 are made of the same material, with the flexible lip 123 preferably being integral to the mounting region 121, i.e. being formed from a single piece of flexible material. In an embodiment as depicted in FIG. 2, the lip 123 may include an edge 123' or may be separated from the space 110 by the edge 123', which edge 123' engages with the subject 1 to reinforce the mounting region 121 in case of the pressure in the space 110 being reduced. The edge 123' may further assist in forming a seal between the ultrasound probe 100 and the subject 1 such that an underpressure can be established in the space 110 as explained above. The mounting region 121 of the probe body 120 may further comprise support portions 124 in between the receiving portions 122 that reinforce the mounting region 121 in case of the pressure in the space 110 being reduced.

The probe body 120 further comprises an inlet 125 and an outlet 127 extending through the probe body 120. For example, at least one of the inlet 125 and the outlet 127 may extend through the lip 123 although it is equally feasible that at least one of the inlet 125 and the outlet 127 extends through the mounting region 121 of the probe body 120. The inlet 125 and the outlet 127 facilitate fluid communication with the sealed space 110 when the ultrasound probe 100 is positioned on the body of the subject 1, e.g. by connecting at least the outlet to an air displacement apparatus such as a fan or pump that draws the fluid in the sealed space 110 from the sealed space 110, which fluid may be replenished through the inlet 125 as will be explained in more detail below. In this manner, the fluid in the sealed space 110 heated by operation of the ultrasound transducer element tiles 130 is periodically or continuously displaced with fluid through the inlet 125 that typically has a lower temperature than the heated fluid in the sealed space 110. Consequently, the ultrasound transducer element tiles 130 are more effectively cooled in this process, which reduces the risk of the ultrasound transducer element tiles 130 overheating. The inlet 125 and/or the outlet 127 may optionally comprise one or more flanges, ribs or the like to facilitate the establishment of a fluid connection, e.g. connection with a pipe, tubing or the like.

Figure 4:
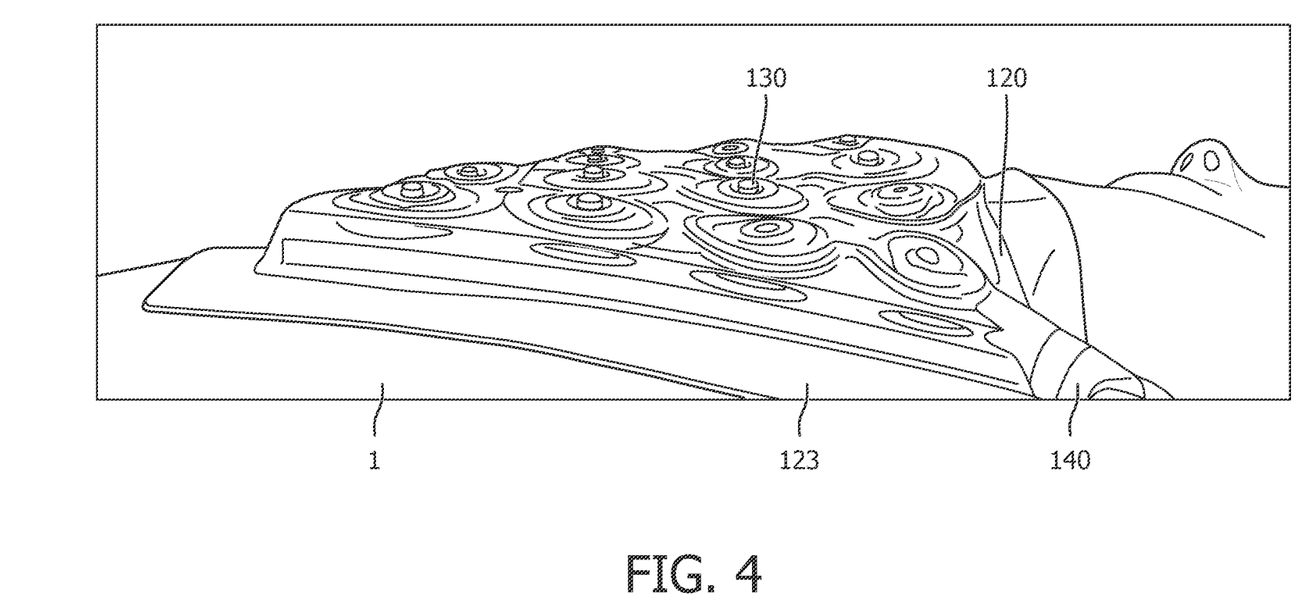
FIG. 4 is an image of an ultrasound probe according to an embodiment deployed on a patient.

FIG. 4 is an image of an example embodiment of an ultrasound probe 100 in the form of a flexible mat positioned on the body of a patient or subject 1. In this embodiment, the probe body 120 is made of an elastomeric material (polyurethane) and includes the lip 123 for hermetically sealing the space in between the ultrasound transducer element tiles 130 and the patient's body as previously explained. A vacuum tube 140 may be attached to outlet 127 of the ultrasound probe 100 to create an underpressure in the space 110 such that the ultrasound transducer element tiles 130 of the ultrasound probe 100 establish a conformal contact with different parts of the body of the subject 1 over a large area.

Figure 5:
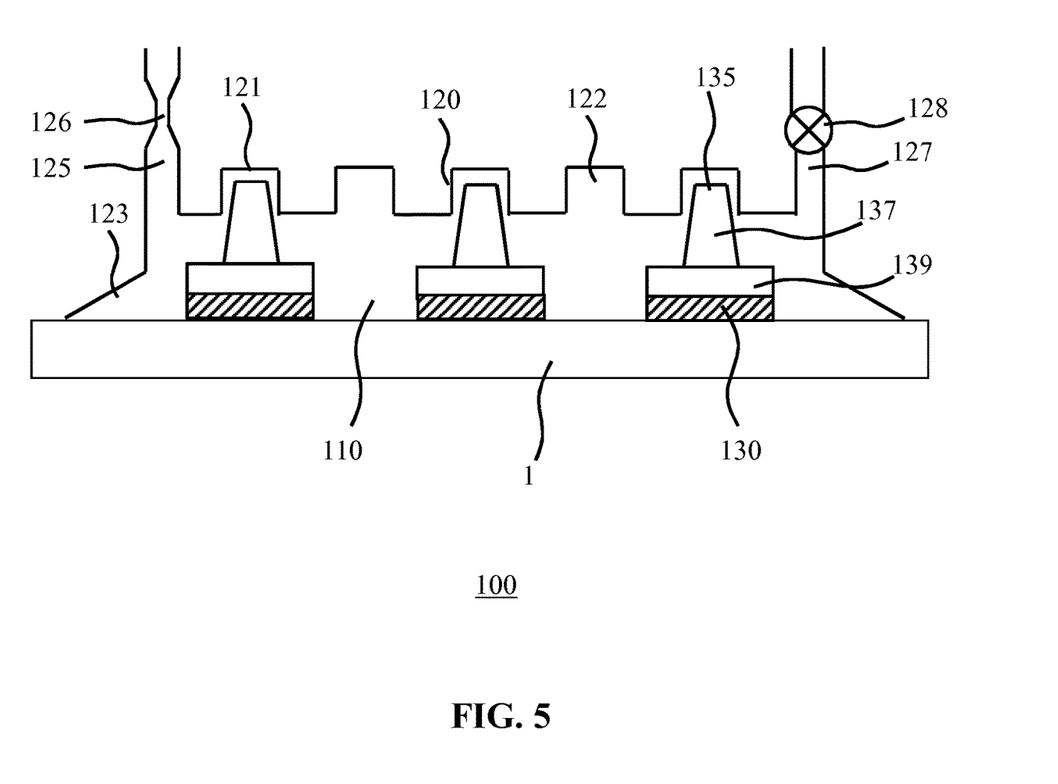
FIG. 5 schematically depicts a cross-sectional view of an ultrasound probe according to another embodiment.

FIG. 5 schematically depicts another embodiment of an ultrasound probe 100.

In this embodiment, the inlet 125 may further comprise a fluid flow regulation structure 126 in order to limit the fluid flow rate into the sealed space 110. This for example may facilitate the generation of an underpressure in the sealed space 110 relative to the ambient pressure upon displacement of the air from the sealed space 110 with an air displacement apparatus as will be explained in more detail below. The fluid flow regulation structure 126 may be implemented as a length of tubing or the like attached to the inlet 125 and comprising a section having a reduced diameter compared to the rest of the tubing in order to achieve the desired fluid flow restriction. Alternatively, a fluid flow regulator, e.g. a valve or the like, may be fluidly connected to the inlet 125. It should be understood that it is not essential that such a fluid flow regulation structure 126 forms an integral part of the inlet 125; it is equally feasible that such a fluid flow regulation structure 126 is integrated in a length of tubing or the like to be connected to the inlet 125. Alternatively or additionally, the outlet 127 may further comprise or may be fluidly attached to a pressure reducing valve 128 arranged to control the pressure in the sealed space 110, e.g. to create a desired underpressure in the sealed space 110 relative to ambient pressure.

Although not specifically shown, it should be understood that the ultrasound probe 100 may comprise additional components that are not necessarily essential to the present invention. For example, the ultrasound probe 100 may further comprise one or more temperature sensors for sensing the temperature of the ultrasound transducer element tiles 130 and to provide a sensor signal indicative of this temperature to the control electronics of the ultrasound probe 100 to facilitate switching of the ultrasound probe 100 to a low power mode in case of potential overheating of the ultrasound transducer element tiles 130. As such additional components are entirely conventional and well-known per se, they are not explained in further detail for the sake of brevity only.

Figure 6:
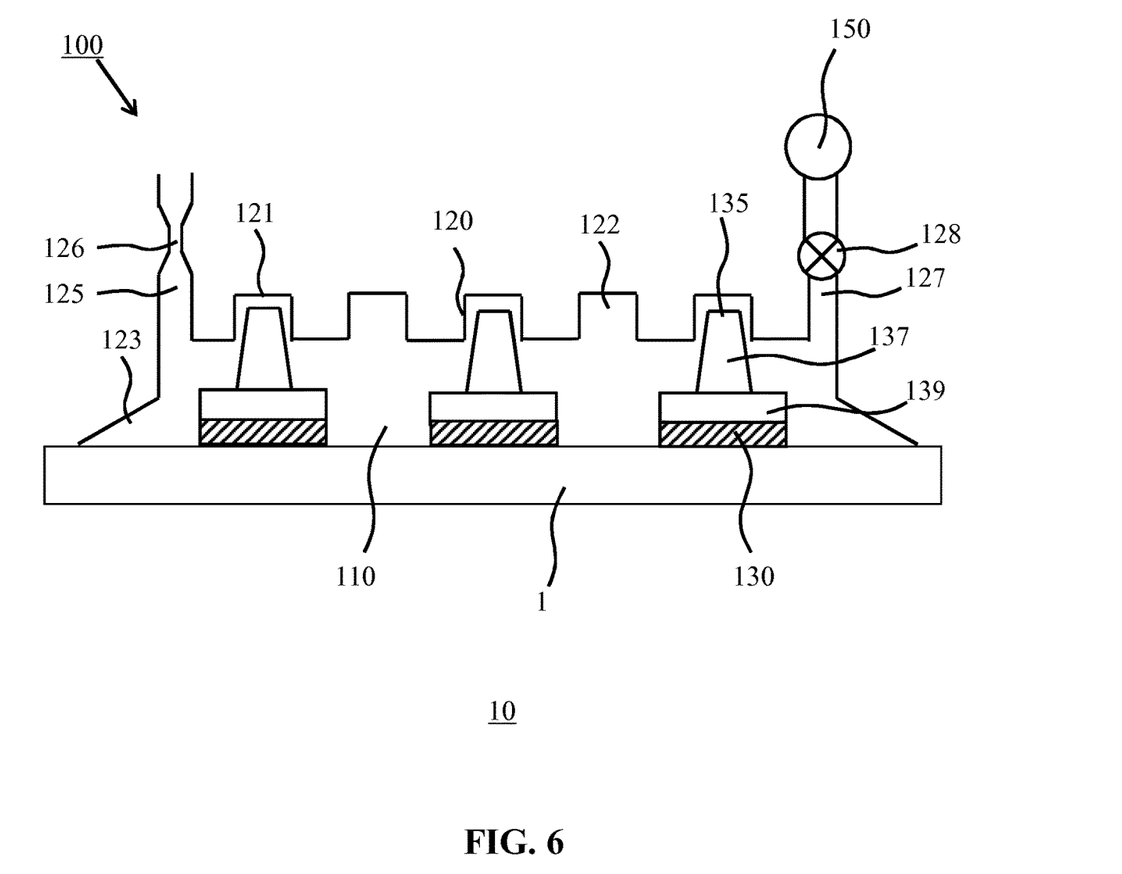
FIG. 6 schematically depicts a cross-sectional view of an aspect of an ultrasound system according to an embodiment.

FIG. 6 schematically depicts an aspect of an ultrasound system 10, specifically a cooling arrangement for cooling the ultrasound transducer element tiles 130 of the ultrasound probe 100. In this embodiment, the outlet 127 of the ultrasound probe 100 is fluidly connected to an air displacement apparatus 150 arranged to draw air from the sealed space 110 during operation of the ultrasound probe 100, e.g. during ultrasound diagnostic imaging or ultrasound therapy. The air drawn from the sealed space 110 by the air displacement apparatus 150 may be replaced with cooler air drawn into the sealed space 110 through the inlet 125 optionally comprising the fluid flow regulation structure 126. The air displacement apparatus 150 may be arranged to generate an underpressure in the sealed space 110 relative to ambient pressure. This for example may be achieved by controlling the fluid influx through the inlet 125, e.g. using the fluid flow regulation structure 126 such that at least at ambient pressure in the sealed space 110, the rate of influx of fluid into the sealed space 110 through the inlet 125 is lower than the rate at which the fluid is drawn from the sealed space 110 by the air displacement apparatus 150 through the outlet 127. As will be readily understood that the skilled person, in such a scenario a stable underpressure will be reached once the rate of influx matches the rate at which the fluid is drawn from the sealed space 110.

The pressure reducing valve 128 may be fluidly connected between the outlet 127 and the air displacement apparatus 150 in order to regulate this underpressure. This for example may be particularly advantageous in case the air displacement apparatus 150 comprises a pump such as a vacuum pump in which case it may not be desirable to lower the pressure in the sealed space 110 in accordance with the full capacity of the pump. In an embodiment, the outlet 127 of the ultrasound probe 100 may be connected to a vacuum pump integral to a dwelling in which the ultrasound system 10 is used, e.g. a hospital or the like, which dwelling may comprise a vacuum network throughout the dwelling to facilitate the connection of multiple devices to the house vacuum, e.g. devices in different rooms of the dwelling. Alternatively, the air displacement apparatus 150 may comprise a fan or the like, which typically implements an operating principle of creating an underpressure upstream from the fan and creating an overpressure downstream from the fan, thereby creating a fluid flow, e.g. an air flow, with the fan. In such an embodiment, the air displacement apparatus 150 can only generate a relatively modest underpressure in the sealed space 110, such that in this embodiment the pressure reducing valve 128 may be omitted.

In the embodiment is schematically depicted in FIG. 6 the fluid volume, e.g. air, extracted from the sealed space 110 with the air displacement apparatus 150 is typically displaced with a different fluid volume, e.g. a fluid volume drawn into the sealed space 110 from ambient through the inlet 125, with the displaced fluid volume typically being discarded, e.g. to ambient. In other words, the embodiment schematically depicted in FIG. 6 is an open cooling system for cooling the ultrasound transducer element tiles 130 of the ultrasound probe 100.

Figure 7:
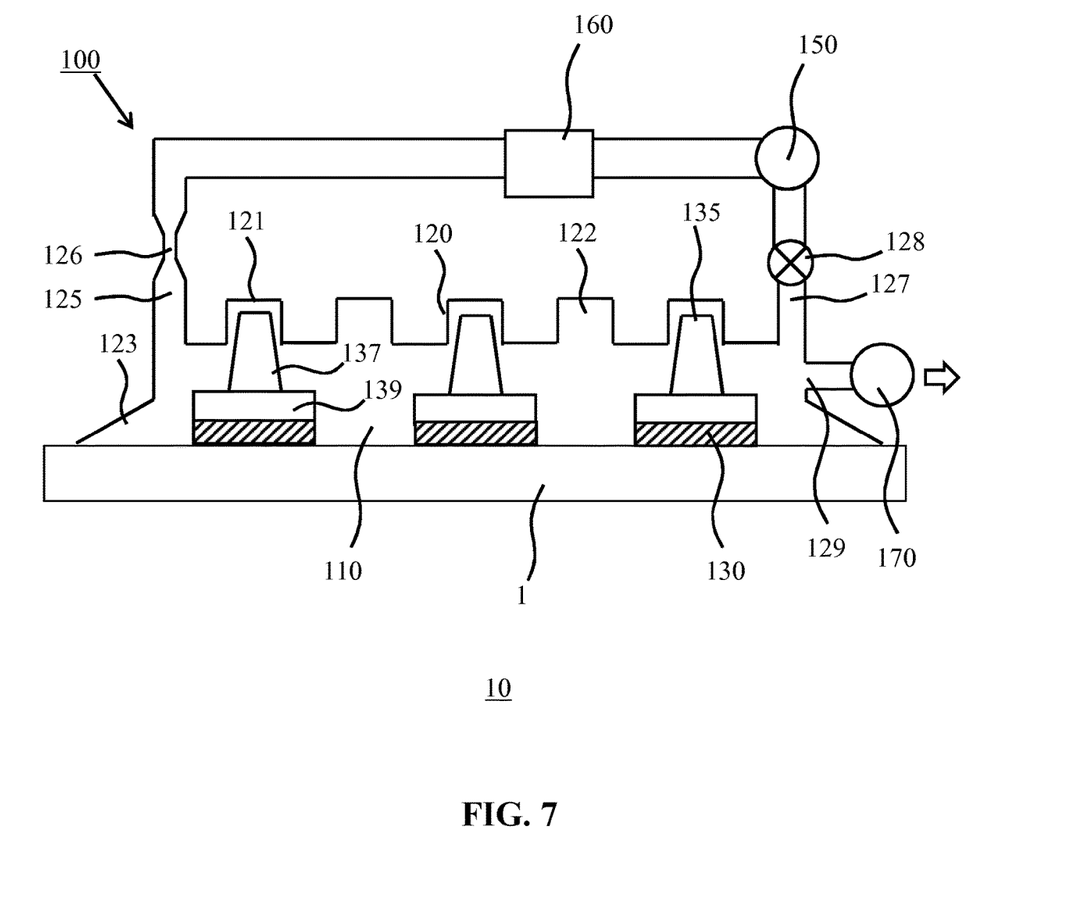
FIG. 7 schematically depicts a cross-sectional view of an aspect of an ultrasound system according to another embodiment.

FIG. 7 schematically depicts an alternative embodiment of a closed cooling system for cooling the ultrasound transducer element tiles 130 of the ultrasound probe 100. In this embodiment, an outlet of the air displacement apparatus 150, e.g. a pump outlet, is fluidly connected to a cooling apparatus 160, a heat exchange apparatus, a refrigerator, or the like, which cooling apparatus 160 has an inlet fluidly connected to the outlet of the air displacement apparatus 150 and has an outlet fluidly connected to the inlet 125 of the ultrasound probe 100. In operation, the air displacement apparatus 150 draws a fluid heated by the ultrasound transducer element tiles 130 from the sealed space 110 through the outlet 127 and delivers the heated fluid to the inlet of the cooling apparatus 160. The heated fluid is cooled by the cooling apparatus 160 and the cooled fluid is subsequently returned by the cooling apparatus to the sealed space 110 through the inlet 125. In this embodiment, the fluid may comprise air or alternatively may comprise an inert gas having desirable heat transfer characteristics, e.g. helium or nitrogen. The air displacement apparatus 150 or the cooling apparatus 160 may be arranged, e.g. may comprise a reservoir containing the inert gas, to insert the inert gas into the closed cooling loop described above. The cooling apparatus 160 may be adapted to evacuate a volume of air from the space 110 to create the underpressure in the space 110 prior to circulating the remaining air (or coolant).

In an alternative embodiment, the ultrasound probe 100 further comprises a further outlet 129 to which a further air displacement apparatus 170 such as a fan or a pump may be connected in order to create the underpressure relative to ambient pressure in the sealed space 110 by evacuating a volume of air from the space 110 as previously explained after which the further outlet 129 may be tied off, e.g. manually or by an automated valve. A pressure sensor (not shown) may be arranged within the space 110, e.g. as part of the probe 100, with the further air displacement apparatus 170 responsive to the pressure sensor such that loss of underpressure, e.g. through air leakage via the lip 123 into the space 110 may be compensated by the further air displacement apparatus 170 to maintain a (more or less) constant underpressure in the space 110.

The further air displacement apparatus 170 may be arranged to exhaust the fluid extracted from the sealed space 110 to ambient or to capture the extracted fluid, e.g. for recycling into the closed cooling loop. At this point, it is noted that although in this embodiment the closed cooling loop is not truly closed due to the further outlet 129 fluidly connected to the further air displacement apparatus 170, the fluid losses through the further outlet 129 during operation of the ultrasound probe 100 may be considered negligibly small, such that this arrangement still approximates a closed system.

Figure 8:
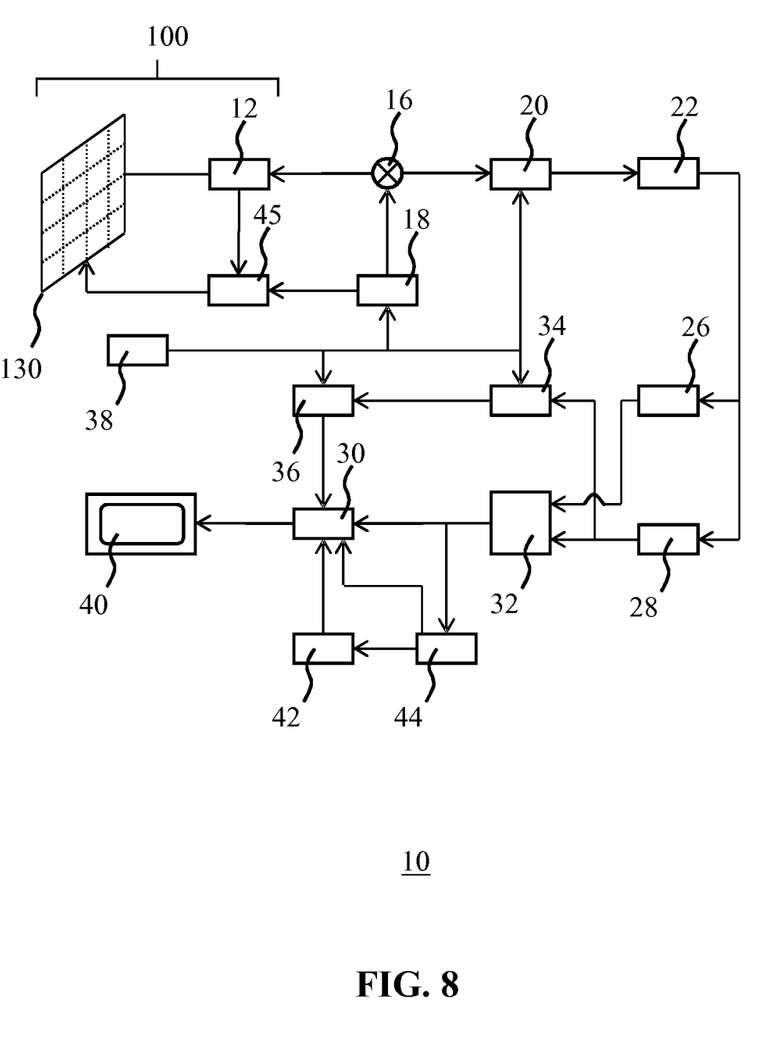
FIG. 8 schematically depicts a block diagram of an ultrasound system according to an example embodiment.

The ultrasound system 10 according to embodiments of the present invention may further comprise electronic circuitry for controlling the ultrasound probe 100 and for processing the ultrasound (pulse) echoes collected by the ultrasound probe 100 in case of an ultrasound diagnostic imaging system 10. Such electronic circuitry may at least partially be housed in a user console or the like as is well-known per se. FIG. 8 shows an example embodiment of the electronics that may be deployed to interface with and control the ultrasound probe 100 for the generation of ultrasound waves, e.g. ultrasound pulses, and reception of ultrasound echoes, e.g. pulse echoes, e.g. for diagnostic imaging purposes. The transducer array may be coupled to a microbeam former 12 in the probe 100 which controls transmission and reception of signals by the ultrasound transducer cells 130. Microbeam formers are capable of at least partial beam forming of the signals received by groups or "patches" of transducer element tiles for instance as described in U.S. Pat. No. 5,997,479 (Savord et al.), U.S. Pat. No. 6,013,032 (Savord), and U.S. Pat. No. 6,623,432 (Powers et al.)

The microbeam former 12 may be coupled by a probe cable, e.g. coaxial wire, to a terminal, e.g. a user console device or the like, comprising a transmit/receive (T/R) switch 16 which switches between transmission and reception modes and protects the main beam former 20 from high energy transmit signals when a microbeam former is not present or used and the transducer array is operated directly by the main system beam former 20. The transmission of ultrasonic beams from the transducer array under control of the microbeam former 12 may be directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the transducer array, or at different angles for a wider field of view. The transducer controller 18 may be coupled to control a voltage source 45 for the ultrasound transducer array. For instance, the voltage source 45 sets the DC and AC bias voltage(s) that are applied to CMUT elements of a CMUT array, e.g. to operate the CMUT elements in collapse mode, as is well-known per se. The transducer controller 18 may be further adapted to control the voltage supply 45 such as to switch the ultrasound transducer element tiles 130 to a low-power mode, e.g. in response to a temperature sensor signal indicative of the ultrasound transducer element tiles 130 reaching a critical temperature.

The partially beam-formed signals produced by the microbeam former 12 may be forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of ultrasound transducer cells 130. In this way the signals received by thousands of transducer elements of a transducer array can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be forwarded to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor 34 produces measures of different flow conditions such as the volume rate of blood flow as well as structural measurements such as the sizes of organs and gestational age. The quantification processor 34 may receive input from the user control panel 38, such as the point in the anatomy of an image where a measurement is to be made.

Output data from the quantification processor 34 is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor 36 receives input from the user control panel 38, such as patient name.

The user control panel 38 is also coupled to the transducer controller 18 to control the generation of ultrasound signals from the transducer array and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system 10 is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound probe 100 may not have 3D imaging capabilities and so on. Other variations will be apparent to the skilled person.

Moreover, it will be understood that the present invention is not limited to an ultrasonic diagnostic imaging system 10. The teachings of the present invention are equally applicable to ultrasonic therapeutic systems, e.g. HIFU ultrasound systems, in which the ultrasound transducer elements of the probe 100 may be operable in transmission mode only as there is no need to receive pulse echoes. As will be immediately apparent to the skilled person, in such therapeutic systems, the system components described with the aid of FIG. 6 and that are required to receive, process and display pulse echoes may be omitted without departing from the teachings of the present application.

It should further be understood that the ultrasound system 10 may comprise additional components such as a controller for controlling the air displacement apparatus 150 and the further air displacement apparatus 170. As this will be immediately apparent to the skilled person, this is not explained in further detail for the sake of brevity only.

Figure 9:
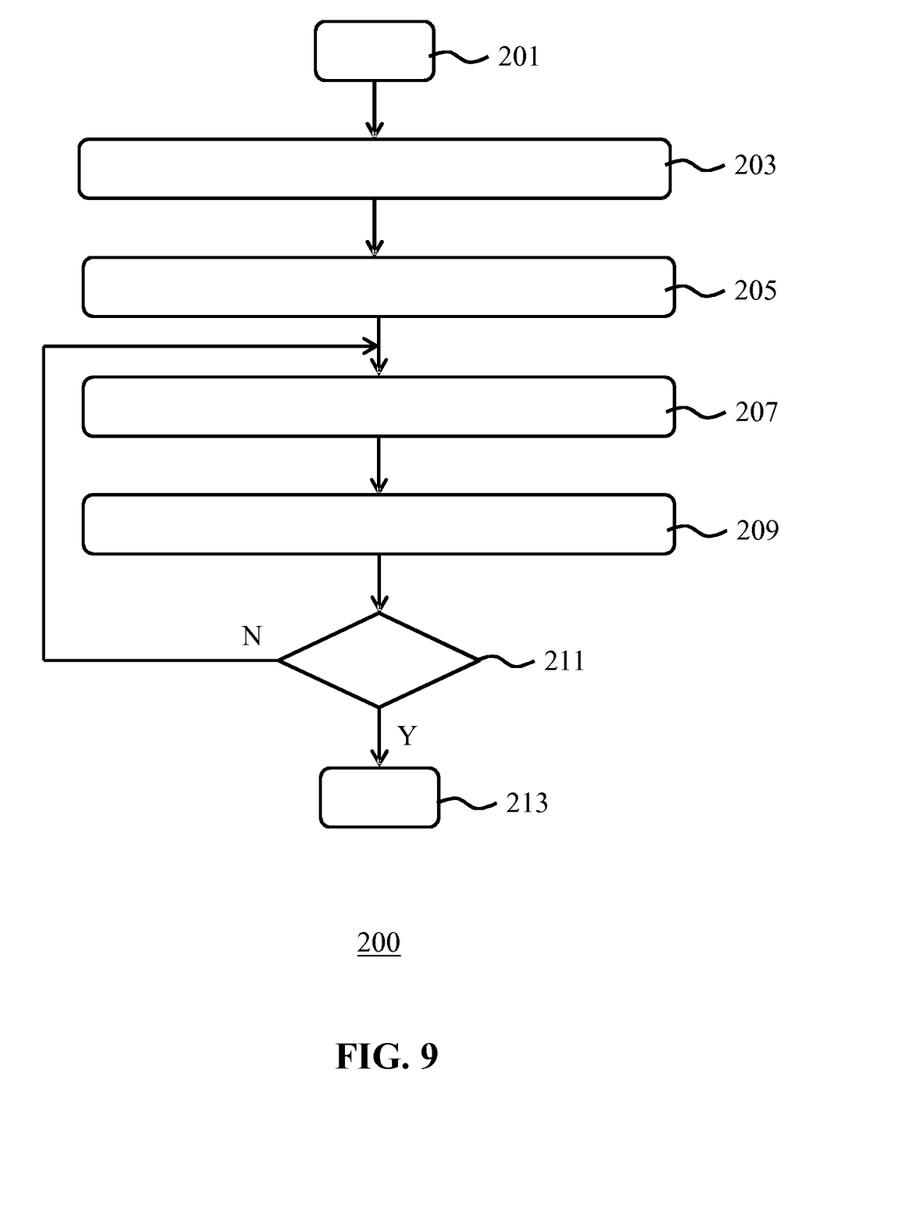
FIG. 9 is a flowchart of a method according to an embodiment.

FIG. 9 is a flow chart of a method 200 of subjecting a subject 1 to ultrasound waves generated with the ultrasound probe 100. Upon initiation of the method 200 in 201, the method 200 proceeds to 203 in which the ultrasound probe 100 is positioned on the subject 1, e.g. on part of the body of the subject 1 such that the space 110 between the mounting area 121 of the probe body 120 carrying the ultrasound transducer element tiles 130 and the subject 1 is hermetically sealed by the flexible lip 123. In an embodiment, an underpressure may be generated in the sealed space 110 in 205 using the air displacement apparatus 150 or the further air displacement apparatus 170, as previously explained.

Next, the ultrasound probe 100 is controlled in 207 to generate the ultrasound waves with the ultrasound transducer element tiles 130 and expose the subject 1 to the generated ultrasound waves, e.g. ultrasound pulses for generating a diagnostic image or highly focused ultrasound waves for ultrasound therapy as mentioned above. At the same time, as indicated in 209, a fluid flow is generated in the sealed space 110 through the inlet 125 and the outlet 127 at least with the air displacement apparatus 150 during the generation of the ultrasound waves to remove fluid from the sealed space 110 that has been heated by the heat generated by the ultrasound transducer element tiles 130. In an embodiment, this may comprise cooling the fluid flow received from the sealed space 110 through the outlet 127, e.g. with the cooling apparatus 160; and returning the cooled fluid flow to the sealed space 110 through the inlet 125. This embodiment may further comprise inserting the fluid into the sealed space 110 prior to cooling, e.g. an inert fluid having desirable heat transfer characteristics such as helium or nitrogen. Preferably, the underpressure in the sealed space 110 is maintained during the generation of the ultrasound waves to ensure a stable conformal contact of the ultrasound probe 100 with the body of the subject 1. It is subsequently checked in 211 if the ultrasound image generation or ultrasound treatment has completed. If this is not the case, the method 200 may revert back to 207; otherwise, the method 200 may terminate in 213.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:
1. An ultrasound probe comprising:
   a probe body having a mounting area and a flexible lip around said mounting area for sealing a space between the mounting area and a part of a subject opposite the mounting area when the subject is contacted by the ultrasound probe to facilitate creation of a reduced pressure in said space;

a plurality of support members disposed in the space, each of the plurality of support members comprising a pillar and a mounting portion coupled to a first end of the pillar, wherein the mounting area comprises a plurality of receiving portions each comprising a cavity configured to accommodate a portion of the pillar of a corresponding one of the plurality of support members, the portion of the pillar including a second end of the pillar, the second end opposite the first end and a length of the pillar is greater than a depth of the cavity;

a plurality of ultrasound transducer element tiles, each of the plurality of ultrasound transducer element tiles mounted to the mounting portion of a corresponding one of the plurality of support members such that the mounting portion is disposed between a corresponding one of the plurality of ultrasound transducer element tiles and a corresponding one of the plurality of receiving portions, wherein each of the plurality of ultrasound transducer tiles comprises at least one transducer element; and wherein the probe body further comprises an inlet and an outlet fluidly connected to the space for facilitating an air flow through said space from the inlet to the outlet when the space is sealed, and wherein, in order to create said reduced pressure upon the outlet being fluidly connected to a fluid displacement apparatus, the inlet is configured to regulate influx of said air flow such that an air flow rate through the inlet is smaller than an air flow rate through the outlet at least at ambient pressure in said space.

2. The ultrasound probe of claim 1, wherein the probe body is flexible.

3. The ultrasound probe of claim 1, wherein at least one of the inlet and the outlet are located in the flexible lip.

4. An ultrasound system comprising the ultrasound probe of claim 1 and the fluid displacement apparatus fluidly connected to the outlet and arranged to generate the air flow through said space when sealed.

5. The ultrasound system of claim 4, wherein the fluid displacement apparatus is a fan or a pump.

6. The ultrasound system of claim 4, further comprising a pressure reducing valve between the outlet and the fluid displacement apparatus.

7. The ultrasound system of claim 4, further comprising a cooling apparatus fluidly connected between the fluid displacement apparatus and the inlet.

8. The ultrasound system of claim 7, wherein the cooling apparatus or the fluid displacement apparatus is adapted to fill the space with the air when sealed.

9. The ultrasound system of claim 7, wherein the probe body comprises a further outlet to said space, the ultrasound system further comprising a further fluid displacement apparatus fluidly connected to the further outlet and adapted to maintain the reduced pressure in said space when sealed.

10. A method of subjecting the subject to ultrasound waves generated with the ultrasound probe of claim 1, the method comprising:
positioning the ultrasound probe on the subject such that the space between the mounting area and the subject is sealed by the flexible lip;
generating the reduced pressure in said sealed space;
generating the ultrasound waves; and
generating the air flow through the inlet to said sealed space and the outlet from said sealed space during the generation of the ultrasound waves.

11. The method of claim 10, further comprising:
cooling the air flow received from the sealed space through the outlet; and
returning the cooled air flow from the cooling to the sealed space through the inlet.

12. The method of claim 11, further comprising inserting an inert fluid into the sealed space prior to cooling the air flow.

13. The method of claim 10, further comprising maintaining the reduced pressure in the sealed space during the generation of the ultrasound waves.

14. The ultrasound probe of claim 1, wherein the inlet comprises a fluid flow regulator for regulating said air flow such that the air flow rate through the inlet is smaller than the air flow rate through the outlet at least at ambient pressure in said space.

15. The ultrasound probe of claim 14, wherein a diameter of the fluid flow regulator is smaller than a diameter of the inlet.

16. The ultrasound probe of claim 1, wherein the flexible lip is integral to the probe body.

17. The ultrasound probe of claim 1, wherein the mounting portions of the plurality of support members are interconnected through a plurality of interconnecting regions.

18. The ultrasound probe of claim 1, wherein the plurality of support members is made of a flexible material comprising a rubber-like material.

19. The ultrasound probe of claim 1, wherein the mounting area further comprises a plurality of mounting support portions between the plurality of receiving portions, wherein the plurality of mounting support portions is configured to reinforce the mounting area.

20. The ultrasound probe of claim 1, wherein a diameter of the second end of the pillar is smaller than a diameter of the second end of the pillar.

21. The ultrasound probe of claim 1, wherein an area of the mounting portion is greater than an area of the first end of the pillar.

* * * * *